United States Patent
Blaschke et al.

(10) Patent No.: US 10,252,970 B2
(45) Date of Patent: *Apr. 9, 2019

(54) METHOD OF DEHYDRATING 3-HYDROXYPROPIONIC ACID TO FORM ACRYLIC ACID

(71) Applicant: BASF SE, Ludwigshafen (DE)

(72) Inventors: Tim Blaschke, Stuttgart (DE); Ortmund Lang, Quirnbach (DE); Nicolai Tonio Wörz, Darmstadt (DE); Christian Raith, Mannheim (DE); Marco Hartmann, Wörth (DE); Marta Zajaczkowski-Fischer, Neuhofen (DE)

(73) Assignee: BASF SE, Ludwigshafen (DE)

( * ) Notice: Subject to any disclaimer, the term of this patent is extended or adjusted under 35 U.S.C. 154(b) by 21 days.

This patent is subject to a terminal disclaimer.

(21) Appl. No.: 15/021,286

(22) PCT Filed: Aug. 21, 2014

(86) PCT No.: PCT/EP2014/067864
§ 371 (c)(1),
(2) Date: Mar. 11, 2016

(87) PCT Pub. No.: WO2015/036218
PCT Pub. Date: Mar. 19, 2015

(65) Prior Publication Data
US 2016/0221916 A1    Aug. 4, 2016

(30) Foreign Application Priority Data

Sep. 12, 2013  (EP) ..................... 13184101

(51) Int. Cl.
*C07C 51/44* (2006.01)
*C07C 57/04* (2006.01)
*C07C 51/377* (2006.01)

(52) U.S. Cl.
CPC ............ *C07C 51/377* (2013.01); *C07C 51/44* (2013.01); *C07C 57/04* (2013.01)

(58) Field of Classification Search
USPC ........................................ 562/599
See application file for complete search history.

(56) References Cited

U.S. PATENT DOCUMENTS

| | | | |
|---|---|---|---|
| 5,154,800 A * | 10/1992 | Berg ............... | C07C 51/44 203/15 |
| 7,538,247 B2 | 5/2009 | Craciun et al. | |
| 9,630,900 B2 * | 4/2017 | Blaschke ............ | C07C 51/377 |
| 2007/0219390 A1 | 9/2007 | Zacher et al. | |
| 2009/0023006 A1 | 1/2009 | Bub et al. | |
| 2011/0105791 A1 | 5/2011 | Kuppinger et al. | |
| 2015/0175517 A1 * | 6/2015 | Yoshida ................ | B01J 27/182 526/75 |
| 2016/0221915 A1 * | 8/2016 | Blaschke ................ | C07C 57/04 |
| 2017/0081268 A1 * | 3/2017 | Blaschke ................ | C07C 51/46 |

FOREIGN PATENT DOCUMENTS

| | | |
|---|---|---|
| EP | 2 56 5212 A1 | 3/2013 |
| EP | 2 565 211 A1 | 3/2013 |
| EP | 2868648 A1 | 5/2015 |
| JP | 2010-180171  * | 8/2010 |
| JP | 2010180171 A | 8/2010 |
| WO | WO-2006/092271 A2 | 9/2006 |
| WO | WO-2007/106099 A1 | 9/2007 |
| WO | WO-2008/023039 A1 | 2/2008 |
| WO | WO-2012/074818 A2 | 6/2012 |
| WO | WO 2014/002886  * | 1/2014 |

OTHER PUBLICATIONS

Merck ("The Merck index: an encyclopedia of chemicals, drugs, and biologicals", online edition <https://www.rsc.org/merck-index>, downloaded on Apr. 1, 2017, compound records for "Methyl tert-Butyl Ether", "Ethyl tert-Butyl Ether", and "Isopropylacetone", p. 1-7).*

Buchholz, Fredric L., et al. *Modern Superabsorbent Polymer Technology*, "Commercial Processes for the Manufacture of Superabsorbent Polymers." New York: John Wiley & Sons, Inc., 1998, pp. 71-103.

International Search Report in international application No. PCT/EP2014/067864, dated Sep. 23, 2014.

* cited by examiner

*Primary Examiner* — Jafar F Parsa
*Assistant Examiner* — Amy C Bonaparte
(74) *Attorney, Agent, or Firm* — Marshall, Gerstein & Borun LLP

(57) ABSTRACT

The invention relates to a process for dehydrating aqueous 3-hydroxypropionic acid to acrylic acid in the liquid phase, wherein aqueous acrylic acid is removed continuously from the liquid phase and the aqueous 3-hydroxypropionic acid and/or the liquid phase have a high content of oligomeric 3-hydroxypropionic acid.

22 Claims, No Drawings

METHOD OF DEHYDRATING 3-HYDROXYPROPIONIC ACID TO FORM ACRYLIC ACID

CROSS-REFERENCE TO RELATED APPLICATIONS

This is the U.S. national phase of International Application No. PCT/EP2014/067864, filed Aug. 21, 2014, which claims the benefit of European Patent application No. 13184101.7, filed Sep. 12, 2013.

The invention relates to a process for dehydrating aqueous 3-hydroxypropionic acid to acrylic acid in the liquid phase, wherein aqueous acrylic acid is removed continuously from the liquid phase and the aqueous 3-hydroxypropionic acid and/or the liquid phase have a high content of oligomeric 3-hydroxypropionic acid.

Because of its very reactive double bond and its carboxylic acid group, acrylic acid is a valuable monomer for preparation of polymers, for example water-absorbing polymer particles, binders for water-based emulsion paints, and adhesives dispersed in aqueous solvent.

Water-absorbing polymer particles are used to produce diapers, tampons, sanitary napkins and other hygiene articles, but also as water-retaining agents in market gardening. The water-absorbing polymer particles are also referred to as superabsorbents.

The production of water-absorbing polymer particles is described in the monograph "Modern Superabsorbent Polymer Technology", F. L. Buchholz and A. T. Graham, Wiley-VCH, 1998, pages 71 to 103.

On the industrial scale, acrylic acid is prepared almost exclusively from fossil raw materials. This is regarded as disadvantageous by the consumers of the hygiene articles. There is therefore a need to produce the water-absorbing polymer particles used in the hygiene articles from renewable raw materials.

One possible route is the fermentative preparation of 3-hydroxypropionic acid and the conversion thereof to acrylic acid. The preparation of 3-hydroxypropionic acid by fermentation is described, for example, in WO 2012/074818 A2.

The dehydration of 3-hydroxypropionic acid in the gas phase is mentioned in U.S. Pat. No. 7,538,247.

The dehydration of 3-hydroxypropionic acid in the liquid phase is mentioned, for example, in WO 2006/092271 A2, WO 2008/023039 A1, JP 2010-180171, EP 2 565 211 A1 and EP 2 565 212 A1.

It was an object of the present invention to provide an improved process for preparing acrylic acid based on renewable raw materials.

The object was achieved by a process for continuously dehydrating aqueous 3-hydroxypropionic acid to aqueous acrylic acid in the liquid phase, the liquid phase having a temperature of 120 to 250° C., aqueous 3-hydroxypropionic acid being continuously added to the liquid phase, and the aqueous acrylic acid being withdrawn continuously from the liquid phase, wherein the ratio of oligomeric 3-hydroxypropionic acid to monomeric 3-hydroxypropionic acid in the aqueous 3-hydroxypropionic acid is at least 1:20 and/or the ratio of oligomeric 3-hydroxypropionic acid to monomeric 3-hydroxypropionic acid in the liquid phase is at least 1:1.

The liquid phase has a temperature of preferably 130 to 220° C., more preferably of 140 to 200° C., most preferably of 150 to 180° C.

The ratio of oligomeric 3-hydroxypropionic acid to monomeric 3-hydroxypropionic acid in the liquid phase is preferably at least 3:1, more preferably at least 5:1, most preferably 10:1. Lower concentrations of monomeric 3-hydroxypropionic acid in the liquid phase, i.e. greater ratios of oligomeric 3-hydroxypropionic acid to monomeric 3-hydroxypropionic acid, facilitate the distillative separation of acrylic acid and 3-hydroxypropionic acid.

The ratio of oligomeric 3-hydroxypropionic acid to monomeric 3-hydroxypropionic acid in the aqueous 3-hydroxypropionic acid (feed) is preferably at least 1:15, more preferably at least 1:10, most preferably 1:5. Lower concentrations of monomeric 3-hydroxypropionic acid in the aqueous 3-hydroxypropionic acid, i.e. greater ratios of oligomeric 3-hydroxypropionic acid to monomeric 3-hydroxypropionic acid, facilitate the enrichment of an oligomeric 3-hydroxypropionic acid in the liquid phase.

The ratio of oligomeric 3-hydroxypropionic acid to monomeric 3-hydroxypropionic acid in the context of this invention is the weight ratio.

The aqueous 3-hydroxypropionic acid used in the process according to the invention comprises preferably at least 10% by weight, more preferably at least 20% by weight and most preferably at least 30% by weight of water.

The liquid phase comprises preferably from 5 to 95% by weight, more preferably from 10 to 90% by weight and most preferably from 20 to 80% by weight of the inert organic solvent 1.

The inert organic solvent 1 has a solubility in water at 23° C. of preferably less than 5 g per 100 ml of water, more preferably less than 1 g per 100 ml of water and most preferably of less than 0.2 g per 100 ml of water.

The boiling point of the inert organic solvent 1 at 1013 mbar is in the range from preferably 200 to 350° C., more preferably from 250 to 320° C., most preferably from 280 to 300° C. Suitable inert organic solvents 1 are, for example, phthalic esters such as dimethyl phthalate and diethyl phthalate, isophthalic esters, such as dimethyl isophthalate and diethyl isophthalate, terephthalic esters such as dimethyl terephthalate and diethyl terephthalate, alkanoic acids such as nonanoic acid and decanoic acid, biphenyl and/or diphenyl ether.

The aqueous acrylic acid formed in the dehydration is preferably removed by distillation. Rectification columns are particularly suitable for this purpose. Through the selection of the separation plates and of the reflux ratio, the content of 3-hydroxypropionic acid in the distillate can be kept low.

Advantageously, a sufficiently long residence time is established in the liquid phase, i.e. the space-time yield should not be too high. Excessively low space-time yields make the process unnecessarily costly. The space-time yield is preferably from 10 to 150 kg/h of acrylic acid, more preferably from 20 to 100 kg/h of acrylic acid, most preferably 30 to 80 kg/h of acrylic acid, in each case per m³ of liquid phase. The space-time yield is the quotient of acrylic acid removed per unit time and the reactor volume.

The residence time in the liquid phase is preferably at least 10 minutes, more preferably at least 30 minutes, most preferably at least 60 minutes. The residence time is the quotient of amount of liquid phase in the dehydration and amount fed in.

Advantageously, a polymerization inhibitor 1 is added to the liquid phase. Suitable polymerization inhibitors 1 are phenothiazine, hydroquinone and/or hydroquinone monomethyl ether. Very particular preference is given to phenothiazine and hydroquinone monomethyl ether. In the case of use of a rectification column, the polymerization inhibitor 1 is metered in at least partly via the reflux.

Advantageously, a polymerization inhibitor 2 is added to the aqueous acrylic acid. Suitable polymerization inhibitors 2 are phenothiazine, hydroquinone and/or hydroquinone monomethyl ether. Very particular preference is given to phenothiazine and hydroquinone monomethyl ether.

The present invention is based on the finding that, under the inventive reaction conditions, 3-hydroxypropionic acid preferentially forms oligomeric 3-hydroxypropionic acid, and oligomeric 3-hydroxypropionic acid can be converted readily to acrylic acid. Avoidance of oligomeric 3-hydroxypropionic acid, as required in WO 2012/091114 A1, is therefore unnecessary.

It has also been found that, surprisingly, the propensity to polymerization can be reduced in the case of use of an inert organic solvent 1. Possibly, the concentration of polymerizable acrylic acid is sufficiently diluted.

Oligomeric 3-hydroxypropionic acid is the product of at least two molecules of 3-hydroxypropionic acid. The two molecules are bonded to one another by esterification of the carboxyl group of one molecule with the hydroxyl group of the other molecule.

Oligomeric acrylic acid is the product of at least two molecules of acrylic acid. The molecules are bonded to one another by Michael addition of the carboxyl group of one molecule with the ethylenic double bond of the other molecule.

The process according to the invention is described hereinafter:

Preparation of 3-Hydroxypropionic Acid

In the process according to the invention, preference is given to using aqueous 3-hydroxypropionic acid produced by fermentation. Such a process is disclosed, for example, in WO 02/090312 A1.

The aqueous 3-hydroxypropionic acid thus produced typically comprises, as well as water, essentially the following constituents:

35 to 70% by weight of 3-hydroxypropionic acid,
0 to 20% by weight of oligomeric 3-hydroxypropionic acid,
0 to 10% by weight of acrylic acid,
0 to 1% by weight of oligomeric acrylic acid,
0.01 to 0.1% by weight of glycolic acid,
0.01 to 0.1% by weight of 2-hydroxypropionic acid,
0.005 to 0.05% by weight of formic acid,
0.005 to 0.05% by weight of acetic acid,
0.005 to 0.05% by weight of succinic acid,
0.005 to 0.05% by weight of fumaric acid,
0.0001 to 0.01% by weight of formaldehyde,
0.0001 to 0.01% by weight of acetaldehyde,
0.0001 to 0.01% by weight of methanol and
0.0001 to 0.01% by weight of ethanol Preparation of Acrylic Acid The dehydration of 3-hydroxypropionic acid is performed in the liquid phase at a temperature of 120 to 300° C., preferably of 150 to 250° C., more preferably of 170 to 230° C., most preferably of 180 to 220° C. The pressure is not subject to any restrictions. A slightly reduced pressure is advantageous for safety reasons.

The liquid phase preferably comprises a polymerization inhibitor 1. Suitable polymerization inhibitors 1 are phenothiazine, hydroquinone and/or hydroquinone monomethyl ether. Very particular preference is given to phenothiazine and hydroquinone monomethyl ether. The liquid phase comprises preferably from 0.001 to 5% by weight, more preferably from 0.01 to 2% by weight and most preferably from 0.1 to 1% by weight of the polymerization inhibitor 1. Advantageously, an oxygen-containing gas is additionally used to inhibit polymerization. Particularly suitable for this purpose are air/nitrogen mixtures having an oxygen content of 6% by volume (lean air).

The liquid phase comprises 5 to 95% by weight, preferably from 10 to 90% by weight, more preferably from 20 to 80% by weight and most preferably from 30 to 60% by weight of the inert organic solvent 1.

The boiling point of the inert organic solvent 1 at 1013 mbar is in the range from preferably 200 to 350° C., more preferably from 250 to 320° C., most preferably from 280 to 300° C. Suitable inert organic solvents 1 are, for example dimethyl phthalate, diethyl phthalate, dimethyl isophthalate, diethyl isophthalate, dimethyl terephthalate, diethyl terephthalate, alkanoic acids such as nonanoic acid and decanoic acid, biphenyl and/or diphenyl ether.

The inert organic solvent 1 has a solubility in water at 23° C. of preferably less than 5 g per 100 ml of water, more preferably less than 1 g per 100 ml of water and most preferably of less than 0.2 g per 100 ml of water.

The dehydration may be base- or acid-catalyzed. Suitable basic catalysts are high-boiling tertiary amines, such as pentamethyldiethylenetriamine. Suitable acidic catalysts are high-boiling inorganic or organic acids, such as phosphoric acid and dodecylbenzenesulfonic acid. "High-boiling" here means a boiling point at 1013 mbar of preferably at least 160° C., more preferably at least 180° C. and most preferably at least 190° C.

The amount of catalyst in the liquid phase is preferably from 1 to 60% by weight, more preferably from 2 to 40% by weight, most preferably from 5 to 20% by weight.

The dehydration is performed continuously. The heat can be supplied via internal and/or external heat exchangers of conventional design and/or via jacket heating (the heat transfer medium used is advantageously steam). The heat is preferably supplied via external circulation evaporators with natural or forced circulation. Particular preference is given to using external circulation evaporators with forced circulation. Evaporators of this kind are described in EP 0 854 129 A1. The use of a plurality of evaporators, connected in series or in parallel, is possible.

If an oxygen-containing gas is used to inhibit polymerization, this is preferably supplied below the evaporator.

The feed to the reactor is preferably preheated to a temperature of 30 to 100° C., more preferably of 40 to 95° C., very particularly of 50 to 90° C.

The water/acrylic acid mixture formed in the dehydration is preferably removed by distillation, more preferably by means of a rectification column 1.

The rectification column 1 is of a design known per se and has the standard internals. The column internals used may in principle be all standard internals, for example trays, structured packings and/or random packings. Among the trays, preference is given to bubble-cap trays, sieve trays, valve trays, Thormann trays and/or dual-flow trays; among the random packings, preference is given to those comprising rings, helices, saddles, Raschig, Intos or Pall rings, Berl or Intalox saddles, or braids. Particular preference is given to dual-flow trays.

In general, from 3 to 10 theoretical plates are sufficient in the rectification column 1. The rectification is typically performed under slightly reduced pressure, preferably at a top pressure of 900 to 980 mbar. The bottom pressure depends on the top pressure, the number and type of column internals and the fluid-dynamic requirements of the rectification.

The rectification column 1 is typically manufactured from austenitic steel, preferably from material 1.4571 (to DIN EN 10020).

The aqueous acrylic acid removed at the top of the rectification column 1 can be cooled indirectly, for example by means of heat exchangers which are known per se to those skilled in the art and are not subject to any particular restriction, or directly, for example by means of a quench. It is preferably cooled by direct cooling. For this purpose, already condensed aqueous acrylic acid is cooled by means of a suitable heat exchanger and the cooled liquid is sprayed in the vapor above the withdrawal point. This spraying can be effected in a separate apparatus or in the rectification unit itself. In the case of spraying in the rectification unit, the withdrawal point for the aqueous acrylic acid advantageously takes the form of a collecting tray. Internals which improve the mixing of the cooled aqueous acrylic acid with the vapor can enhance the effect of the direct cooling. All standard internals are useful in principle for this purpose, for example trays, structured packings and/or random packings. Among the trays, preference is given to bubble-cap trays, sieve trays, valve trays, Thormann trays and/or dual-flow trays. Among the random packings, preference is given to those comprising rings, helices, saddles, Raschig, Intos or Pall rings, Berl or Intalox saddles, or braids. Particular preference is given to dual-flow trays. In general, 2 to 5 theoretical plates are sufficient here. These trays are not included in the figures given so far for the number of theoretical plates in the rectification column 1. The direct condensation of the aqueous acrylic acid can also be executed in more than one stage, with temperature decreasing in the upward direction.

In the case of use of a water-insoluble inert organic solvent 1, the condensed distillate from the rectification column 1 is separated by means of a phase separator. The organic phase can be recycled into the rectification column 1, for example into the bottom. The aqueous phase can likewise be partly recycled into the rectification column 1, for example as reflux and for direct cooling of the vapor.

The aqueous acrylic acid removed via the top of the rectification column 1 typically comprises, as well as water and traces of the inert organic solvent 1, essentially the following constituents:
  0 to 0.001% by weight of 3-hydroxypropionic acid,
  0 to 0.001% by weight of oligomeric 3-hydroxypropionic acid,
  20 to 80% by weight of acrylic acid,
  0 to 0.001% by weight of oligomeric acrylic acid,
  0.001 to 1% by weight of glycolic acid,
  0 to 0.001% by weight of 2-hydroxypropionic acid,
  0.001 to 1% by weight of formic acid,
  0.001 to 1% by weight of acetic acid,
  0 to 0.001% by weight of succinic acid,
  0 to 0.001% by weight of fumaric acid,
  0.0001 to 0.05% by weight of formaldehyde,
  0.0001 to 0.05% by weight of acetaldehyde,
  0.0001 to 0.05% by weight of methanol and
  0.0001 to 0.05% by weight of ethanol A portion of the aqueous acrylic acid withdrawn, preferably 10 to 40% by weight based on the total amount of distillate, is used as reflux; the remainder of the aqueous acrylic acid is discharged.

The aqueous acrylic acid obtained in the dehydration can be worked up in an extraction column.

Advantageously, a portion of the liquid phase is withdrawn from the reactor, washed with water and, after phase separation, recycled. The aqueous phase thus obtained can be discarded or, after further purification steps, sent to the extraction column together with the aqueous acrylic acid withdrawn at the top of the rectification column 1.

The extraction column is of a design known per se and may have the standard internals. Useful column internals in principle include all standard internals. Examples are trays, structured packings and/or random packings. Among the trays, preference is given to sieve trays and/or dual-flow trays. Among the random packings, preference is given to those comprising rings, helices, saddles, Raschig, Intos or Pall rings, Berl or Intalox saddles, or braids. Particular preference is given to dual-flow trays. In general, 10 to 25 theoretical plates are sufficient here.

The extraction column is operated at a temperature of preferably 30 to 70° C., more preferably 40 to 60° C., most preferably 45 to 55° C.

In the extraction column, acrylic acid is extracted from the aqueous phase by means of an inert organic solvent 2. The boiling point of the inert organic solvent 2 at 1013 mbar is in the range from preferably 200 to 350° C., more preferably from 250 to 320° C., most preferably from 280 to 300° C. Suitable inert organic solvents 2 are, for example, phthalic esters such as dimethyl phthalate and diethyl phthalate, isophthalic esters such as dimethyl isophthalate and diethyl isophthalate, terephthalic esters such as dimethyl terephthalate and diethyl terephthalate, alkanoic acids such as nonanoic acid and decanoic acid, biphenyl and/or diphenyl ether.

The inert organic solvent 2 has a solubility in water at 23° C. of preferably less than 5 g per 100 ml of water, more preferably less than 1 g per 100 ml of water and most preferably of less than 0.2 g per 100 ml of water.

In a particularly preferred embodiment of the present invention, the inert organic solvent 1 is also used as the inert organic solvent 2. In this case, the phase separator at the top of the rectification column 1 can be dispensed with.

The ratio of aqueous phase (aqueous acrylic acid) and organic phase (inert organic solvent 2) is preferably from 0.5:1 to 1.5:1. To maintain the ratio, a portion of the aqueous extract can be recycled into the extraction column.

The aqueous extract removed at the top of the extraction column can be discarded and typically comprises, as well as water and traces of the inert organic solvent and of any catalyst used, essentially the following constituents:
  0.005 to 0.1% by weight of 3-hydroxypropionic acid,
  0.05 to 1% by weight of oligomeric 3-hydroxypropionic acid,
  0.1 to 2% by weight of acrylic acid,
  0.1 to 2% by weight of oligomeric acrylic acid,
  0.01 to 1% by weight of glycolic acid,
  0.01 to 1% by weight of 2-hydroxypropionic acid,
  0.01 to 0.2% by weight of formic acid,
  0.005 to 0.1% by weight of acetic acid,
  0.01 to 0.2% by weight of succinic acid,
  0.01 to 0.2% by weight of fumaric acid,
  0.002% by weight of formaldehyde,
  0 to 0.001% by weight of acetaldehyde,
  0.0002 to 0.01% by weight of methanol and
  0 to 0.002% by weight of ethanol The organic extract removed at the base of the extraction column typically comprises, as well as the inert organic solvents and any catalyst, essentially the following constituents:
  0.0005 to 0.01% by weight of 3-hydroxypropionic acid, 0.01 to 1% by weight of oligomeric 3-hydroxypropionic acid,
1 to 5% by weight of water,
10 to 35% by weight of acrylic acid,
0.01 to 1% by weight of oligomeric acrylic acid,
0.005 to 0.5% by weight of glycolic acid,
0.005 to 0.2% by weight of 2-hydroxypropionic acid,
0.0001 to 0.1% by weight of formic acid,
0.001 to 0.1% by weight of acetic acid,
0.001 to 0.05% by weight of succinic acid,
0.001 to 0.1% by weight of fumaric acid,
0.0001 to 0.01% by weight of formaldehyde,
0.0001 to 0.005% by weight of acetaldehyde,
0.0001 to 0.005% by weight of methanol and
0.0001 to 0.01% by weight of ethanol The organic extract obtained in the extraction can be worked up in a rectification column 2.

The rectification column 2 is of a design known per se and has the standard internals. The column internals used may in principle be all standard internals, for example trays, structured packings and/or random packings. Among the trays, preference is given to bubble-cap trays, sieve trays, valve trays, Thormann trays and/or dual-flow trays; among the random packings, preference is given to those comprising rings, helices, saddles, Raschig, Intos or Pall rings, Berl or Intalox saddles, or braids. Particular preference is given to dual-flow trays.

In general, from 10 to 25 theoretical plates are sufficient in the rectification unit. The rectification is typically performed under reduced pressure, preferably at a top pressure of 70 to 140 mbar. The bottom pressure depends on the top pressure, the number and type of column internals and the fluid-dynamic requirements of the rectification, and is preferably 200 to 400 mbar.

The reflux of the rectification column 2 preferably comprises a polymerization inhibitor 2. Suitable polymerization inhibitors 2 are phenothiazine, hydroquinone and/or hydroquinone monomethyl ether. Very particular preference is given to phenothiazine. The reflux comprises preferably from 0.0005 to 1% by weight, more preferably from 0.002 to 0.5% by weight and most preferably from 0.01 to 0.1% by weight of the polymerization inhibitor 1. Advantageously, an oxygen-containing gas is additionally used to inhibit polymerization. Particularly suitable for this purpose are air/nitrogen mixtures having an oxygen content of 6% by volume (lean air).

The rectification column 2 is typically manufactured from austenitic steel, preferably from material 1.4571 (to DIN EN 10020).

The feed into the rectification column 2 is appropriately effected in the lower region thereof. It is preferably effected 2 to 5 theoretical plates above the bottom of the rectification column 2. The feed temperature is preferably from 20 to 200° C., more preferably from 50 to 180° C. and most preferably from 80 to 160° C.

The heat is supplied via internal and/or external heat exchangers (the heat transfer medium is again preferably steam) of conventional design and/or via jacket heating. The heat is preferably supplied via external circulation evaporators with natural or forced circulation. Particular preference is given to external circulation evaporators with forced circulation. Evaporators of this kind are described in EP 0 854 129 A1. The use of a plurality of evaporators, connected in series or in parallel, is possible. Preference is given to operating 2 to 4 evaporators in parallel. The bottom temperature of the rectification column 2 is typically 180 to 250° C., preferably 195 to 235° C.

If an oxygen-containing gas is used to inhibit polymerization, this is preferably supplied below the evaporator.

The high boiler fraction obtained in the bottoms of the rectification column 2 typically comprises, as well as the inert organic solvents and any catalyst, essentially the following constituents:
0.001 to 0.05% by weight of 3-hydroxypropionic acid,
0.01 to 1% by weight of oligomeric 3-hydroxypropionic acid,
0 to 0.0005% by weight of water,
0.01 to 1% by weight of acrylic acid,
0.01 to 1% by weight of oligomeric acrylic acid,
0.005 to 0.2% by weight of glycolic acid,
0.005 to 0.2% by weight of 2-hydroxypropionic acid,
0 to 0.0005% by weight of formic acid,
0 to 0.0005% by weight of acetic acid,
0.001 to 0.05% by weight of succinic acid,
0.001 to 0.1% by weight of fumaric acid,
0 to 0.0005% by weight of formaldehyde,
0 to 0.0005% by weight of acetaldehyde,
0 to 0.0005% by weight of methanol and
0 to 0.0005% by weight of ethanol The bottoms liquid which comprises the inert organic solvent 2 and is withdrawn from the rectification column 2 is recycled via a heat exchanger into the top region of the extraction column. The bottoms liquid is preferably conducted via a solids separator (cyclone) and optionally supplemented with fresh inert organic solvent 2.

Above the feed into the rectification column 2, a crude acrylic acid is withdrawn via a side draw, preferably 8 to 20 theoretical plates above the column bottom. The withdrawal of the crude acrylic acid is effected in a customary manner and is not subject to any restriction. A suitable removal method is via a collecting tray, in which case the entire reflux is collected and a portion is discharged and the other portion is used as reflux below the collecting tray, or via a tray with integrated removal means, preferably via a dual-flow tray with integrated removal means.

The crude acrylic acid withdrawn typically comprises, as well as acrylic acid, essentially the following constituents:
0 to 0.0005% by weight of 3-hydroxypropionic acid,
0 to 0.0005% by weight of oligomeric 3-hydroxypropionic acid,
0 to 5% by weight of water,
0 to 0.0005% by weight of oligomeric acrylic acid,
0.001 to 0.02% by weight of glycolic acid,
0 to 0.0005% by weight of 2-hydroxypropionic acid,
0.005 to 0.01% by weight of formic acid,
0.01 to 0.2% by weight of acetic acid,
0 to 0.0005% by weight of succinic acid,
0 to 0.0005% by weight of fumaric acid,
0 to 0.0005% by weight of formaldehyde,
0 to 0.0005% by weight of acetaldehyde,
0 to 0.005% by weight of methanol and
0 to 0.005% by weight of ethanol The crude acrylic acid withdrawn is cooled by means of a heat exchanger (an example of a suitable coolant is surface water). The use of a plurality of heat exchangers, connected in series or in parallel, is possible. In the heat exchangers, which are known per se to those skilled in the art and are not subject to any particular restriction, the crude acrylic acid is preferably cooled to 40 to 90° C.

The crude acrylic acid withdrawn is discharged and some is used as solvent for the polymerization inhibitor 2.

The low boiler stream removed at the top of the rectification column 2 can be cooled indirectly, for example by means of heat exchangers (the coolant used may, for example, be surface water) which are known per se to those skilled in the art and are not subject to any particular restriction, or directly, for example by means of a quench. It is preferably removed by direct cooling. For this purpose, already condensed low boiler fraction is cooled by means of a suitable heat exchanger and the cooled liquid is sprayed in the vapor above the withdrawal point. This spraying can be effected in a separate apparatus or in the rectification column 2 itself. In the case of spraying in the rectification column 2, the withdrawal point for the low boiler fraction advantageously takes the form of a collecting tray. Internals which improve the mixing of the cooled low boiler fraction with the vapor can enhance the effect of the direct cooling. All standard internals are useful in principle for this purpose, for example trays, structured packings and/or random packings. Among the trays, preference is given to bubble-cap trays, sieve trays, valve trays, Thormann trays and/or dual-flow trays. Among the random packings, preference is given to those comprising rings, helices, saddles, Raschig, Intos or Pall rings, Berl or Intalox saddles, or braids. Particular preference is given to dual-flow trays. In general, 2 to 5 theoretical plates are sufficient here. These trays are not included in the figures given so far for the number of theoretical plates in the rectification column 2. The direct condensation of the low boiler fraction can also be executed in more than one stage, with temperature decreasing in the upward direction.

The low boiler stream removed via the top of the rectification column 2 typically comprises, as well as water, essentially the following constituents:

0 to 0.0005% by weight of 3-hydroxypropionic acid,
0 to 0.0005% by weight of oligomeric 3-hydroxypropionic acid,
10 to 60% by weight of acrylic acid,
0 to 0.0005% by weight of oligomeric acrylic acid,
0 to 0.0005% by weight of glycolic acid,
0 to 0.0005% by weight of 2-hydroxypropionic acid,
0.01 to 1% by weight of formic acid,
0.01 to 1% by weight of acetic acid,
0 to 0.0005% by weight of succinic acid,
0 to 0.0005% by weight of fumaric acid,
0.0005 to 0.02% by weight of formaldehyde,
0.0001 to 0.01% by weight of acetaldehyde,
0.0005 to 0.02% by weight of methanol and
0.005 to 0.05% by weight of ethanol A portion of the liquid withdrawn as low boiler fraction is used as reflux; the remainder of the low boiler fraction is discharged and recycled as aqueous phase into the extraction column.

The crude acrylic acid withdrawn from the rectification column 2 can be used directly for production of water-absorbing polymer particles. Preference is given to further purifying the crude acrylic acid by crystallization. The mother liquor obtained in the crystallization can be recycled into the rectification column 2, preferably below the removal point for the crude acrylic acid.

The crude acrylic acid can be purified by layer crystallization, as described, for example, in EP 0 616 998 A1, or by suspension crystallization, as described in DE 100 39 025 A1. Suspension crystallization is preferred. The combination of a suspension crystallization with a wash column, as described in WO 2003/041832 A1, is particularly preferred.

The acrylic acid thus purified typically comprises, as well as acrylic acid, essentially the following constituents:

<0.0001% by weight of 3-hydroxypropionic acid,
<0.0001% by weight of oligomeric 3-hydroxypropionic acid,
0.01 to 0.05% by weight of water,
<0.0001% by weight of oligomeric acrylic acid,
<0.0001% by weight of glycolic acid,
<0.0001% by weight of 2-hydroxypropionic acid,
<0.0001% by weight of formic acid,
0.01 to 0.05% by weight of acetic acid,
<0.0001% by weight of succinic acid,
<0.0001% by weight of fumaric acid,
<0.0001% by weight of formaldehyde,
<0.0001% by weight of acetaldehyde,
<0.0001% by weight of methanol and
<0.0001% by weight of ethanol The acrylic acid prepared by the process according to the invention can be used for preparation of acrylic esters such as methyl acrylate, ethyl acrylate, n-butyl acrylate and 2-ethylhexyl acrylate, and for preparation of polymers such as water-absorbing polymer particles.

Production of Water-Absorbing Polymer Particles

Water-absorbing polymer particles are produced by polymerizing a monomer solution or suspension comprising
a) at least one ethylenically unsaturated monomer which bears acid groups and may be at least partly neutralized, especially partly neutralized acrylic acid,
b) at least one crosslinker,
c) at least one initiator,
d) optionally one or more ethylenically unsaturated monomers copolymerizable with the monomers mentioned under a) and
e) optionally one or more water-soluble polymers,
and are typically water-insoluble.

The monomers a) are preferably water-soluble, i.e. the solubility in water at 23° C. is typically at least 1 g/100 g of water, preferably at least 5 g/100 g of water, more preferably at least 25 g/100 g of water and most preferably at least 35 g/100 g of water.

Suitable monomers a) are, for example, ethylenically unsaturated carboxylic acids, such as acrylic acid, methacrylic acid and itaconic acid. Further suitable monomers a) are, for example, ethylenically unsaturated sulfonic acids, such as styrenesulfonic acid and 2-acrylamido-2-methylpropanesulfonic acid (AMPS).

The proportion of acrylic acid and/or salts thereof in the total amount of monomers a) is preferably at least 50 mol %, more preferably at least 90 mol %, most preferably at least 95 mol %.

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and DE 103 31 450

A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/032962 A2.

Preferred crosslinkers b) are pentaerythrityl triallyl ether, tetraallyloxyethane, methylenebismethacrylamide, 15-tuply ethoxylated trimethylolpropane triacrylate, polyethylene glycol diacrylate, trimethylolpropane triacrylate and triallylamine.

Very particularly preferred crosslinkers b) are the polyethoxylated and/or -propoxylated glycerols which have been esterified with acrylic acid or methacrylic acid to give di- or triacrylates, as described, for example, in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably 0.05 to 1.5% by weight, more preferably 0.1 to 1% by weight, most preferably 0.2 to 0.5% by weight, based in each case on monomer a). With rising crosslinker content, the centrifuge retention capacity (CRC) falls and the absorption under a pressure of 21.0 g/cm$^2$ passes through a maximum.

The initiators c) used may be all compounds which generate free radicals under the polymerization conditions, for example thermal initiators, redox initiators or photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. The reducing component used is, however, preferably a mixture of the sodium salt of 2-hydroxy-2-sulfinatoacetic acid, the disodium salt of 2-hydroxy-2-sulfonatoacetic acid and sodium bisulfite. Such mixtures are obtainable as Bruggolite® FF6 and Bruggolite® FF7 (Bruggemann Chemicals; Heilbronn; Germany).

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

The water-soluble polymers e) used may be polyvinyl alcohol, polyvinylpyrrolidone, starch, starch derivatives, modified cellulose, such as methyl cellulose or hydroxyethyl cellulose, gelatin, polyglycols or polyacrylic acids, preferably starch, starch derivatives and modified cellulose.

Typically, an aqueous monomer solution is used. The water content of the monomer solution is preferably from 40 to 75% by weight, more preferably from 45 to 70% by weight and most preferably from 50 to 65% by weight. It is also possible to use monomer suspensions, i.e. monomer solutions with excess monomer a), for example sodium acrylate. With rising water content, the energy requirement in the subsequent drying rises, and, with falling water content, the heat of polymerization can only be removed inadequately.

For optimal action, the polymerization inhibitors typically used in acrylic acid require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

Suitable reactors are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on a belt is described, for example, in DE 38 25 366 A1 and U.S. Pat. No. 6,241,928. Polymerization in a belt reactor forms a polymer gel which has to be comminuted in a further process step, for example in an extruder or kneader.

To improve the drying properties, the comminuted polymer gel obtained by means of a kneader can additionally be extruded.

However, it is also possible to dropletize an aqueous monomer solution and to polymerize the droplets obtained in a heated carrier gas stream. It is possible here to combine the process steps of polymerization and drying, as described in WO 2008/040715 A2, WO 2008/052971 A1 and WO 2011/026876 A1.

The acid groups of the resulting polymer gels have typically been partially neutralized. Neutralization is preferably carried out at the monomer stage. This is typically accomplished by mixing in the neutralizing agent as an aqueous solution or preferably also as a solid. The degree of neutralization is preferably from 25 to 95 mol %, more preferably from 30 to 80 mol % and most preferably from 40 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof.

However, it is also possible to carry out neutralization after the polymerization, at the stage of the polymer gel formed in the polymerization. It is also possible to neutralize up to 40 mol %, preferably 10 to 30 mol % and more preferably 15 to 25 mol % of the acid groups before the polymerization by adding a portion of the neutralizing agent directly to the monomer solution and setting the desired final degree of neutralization only after the polymerization, at the polymer gel stage. When the polymer gel is at least partly neutralized after the polymerization, the polymer gel is preferably comminuted mechanically, for example by means of an extruder, in which case the neutralizing agent can be sprayed, sprinkled or poured on and then carefully mixed in. To this end, the gel mass obtained can be repeatedly extruded for homogenization.

The polymer gel is then preferably dried with a belt drier until the residual moisture content is preferably 0.5 to 15% by weight, more preferably 1 to 10% by weight and most preferably 2 to 8% by weight, the residual moisture content being determined by EDANA recommended test method No. WSP 230.2-05 "Mass Loss Upon Heating". In the case of too high a residual moisture content, the dried polymer gel has too low a glass transition temperature $T_g$ and can be processed further only with difficulty. In the case of too low a residual moisture content, the dried polymer gel is too brittle and, in the subsequent comminution steps, undesirably large amounts of polymer particles with an excessively low particle size are obtained ("fines"). The solids content of the gel before the drying is preferably from 25 to 90% by weight, more preferably from 35 to 70% by weight and most preferably from 40 to 60% by weight. However, a fluidized bed drier or a paddle drier may optionally also be used for drying purposes.

Thereafter, the dried polymer gel is ground and classified, and the apparatus used for grinding may typically be single or multistage roll mills, preferably two- or three-stage roll mills, pin mills, hammer mills or vibratory mills.

The mean particle size of the polymer particles removed as the product fraction is preferably at least 200 μm, more preferably from 250 to 600 μm and very particularly from 300 to 500 μm. The mean particle size of the product fraction may be determined by means of EDANA recommended test method No. WSP 220.2-05 "Particle Size Distribution", where the proportions by mass of the screen fractions are plotted in cumulated form and the mean particle size is determined graphically. The mean particle size here is the value of the mesh size which gives rise to a cumulative 50% by weight.

The proportion of particles having a particle size of greater than 150 μm is preferably at least 90% by weight, more preferably at least 95% by weight and most preferably at least 98% by weight.

Polymer particles with too small a particle size lower the permeability (SFC). The proportion of excessively small polymer particles ("fines") should therefore be low.

Excessively small polymer particles are therefore typically removed and recycled into the process. This is preferably done before, during or immediately after the polymerization, i.e. before the drying of the polymer gel. The excessively small polymer particles can be moistened with water and/or aqueous surfactant before or during the recycling.

It is also possible to remove excessively small polymer particles in later process steps, for example after the surface postcrosslinking or another coating step. In this case, the excessively small polymer particles recycled are surface postcrosslinked or coated in another way, for example with fumed silica.

If a kneading reactor is used for polymerization, the excessively small polymer particles are preferably added during the last third of the polymerization.

If the excessively small polymer particles are added at a very late stage, for example not until an apparatus connected downstream of the polymerization reactor, for example an extruder, the excessively small polymer particles can be incorporated into the resulting polymer gel only with difficulty. Insufficiently incorporated, excessively small polymer particles are, however, detached again from the dried polymer gel during the grinding, are therefore removed again in the course of classification and increase the amount of excessively small polymer particles to be recycled.

The proportion of particles having a particle size of at most 850 μm is preferably at least 90% by weight, more preferably at least 95% by weight, most preferably at least 98% by weight.

The proportion of particles having a particle size of at most 600 μm is preferably at least 90% by weight, more preferably at least 95% by weight, most preferably at least 98% by weight.

Polymer particles of excessively large particle size lower the free swell rate. The proportion of excessively large polymer particles should therefore likewise be low.

Excessively large polymer particles are therefore typically removed and recycled into the grinding of the dried polymer gel.

To further improve the properties, the polymer particles can be surface postcrosslinked. Suitable surface postcrosslinkers are compounds which comprise groups which can form covalent bonds with at least two carboxylate groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

Additionally described as suitable surface postcrosslinkers are cyclic carbonates in DE 40 20 780 C1, 2-oxazolidinone and derivatives thereof, such as 2-hydroxyethyl-2-oxazolidinone, in DE 198 07 502 A1, bis- and poly-2-oxazolidinones in DE 198 07 992 C1, 2-oxotetrahydro-1,3-oxazine and derivatives thereof in DE 198 54 573 A1, N-acyl-2-oxazolidinones in DE 198 54 574 A1, cyclic ureas in DE 102 04 937 A1, bicyclic amido acetals in DE 103 34 584 A1, oxetanes and cyclic ureas in EP 1 199 327 A2 and morpholine-2,3-dione and derivatives thereof in WO 2003/031482 A1.

Preferred surface postcrosslinkers are ethylene carbonate, ethylene glycol diglycidyl ether, reaction products of polyamides with epichlorohydrin and mixtures of propylene glycol and 1,4-butanediol.

Very particularly preferred surface postcrosslinkers are 2-hydroxyethyl-2-oxazolidinone, 2-oxazolidinone and 1,3-propanediol.

In addition, it is also possible to use surface postcrosslinkers which comprise additional polymerizable ethylenically unsaturated groups, as described in DE 37 13 601 A1.

The amount of surface postcrosslinker is preferably 0.001 to 5% by weight, more preferably 0.02 to 2% by weight and most preferably 0.05 to 1% by weight, based in each case on the polymer particles.

In a preferred embodiment of the present invention, polyvalent cations are applied to the particle surface in addition to the surface postcrosslinkers before, during or after the surface postcrosslinking.

The polyvalent cations usable in the process according to the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium. Possible counterions are hydroxide, chloride, bromide, sulfate, hydrogensulfate, carbonate, hydrogencarbonate, nitrate, phosphate, hydrogenphosphate, dihydrogenphosphate and carboxylate, such as acetate, citrate and lactate. Salts with different counterions are also possible, for example basic aluminum salts such as aluminum monoacetate or aluminum monolactate. Aluminum sulfate, aluminum monoacetate and aluminum lactate are preferred. Apart from metal salts, it is also possible to use polyamines as polyvalent cations.

The amount of polyvalent cation used is, for example, 0.001 to 1% by weight, preferably 0.005 to 0.5% by weight and more preferably 0.02 to 0.2% by weight, based in each case on the polymer particles.

The surface postcrosslinking is typically performed in such a way that a solution of the surface postcrosslinker is sprayed onto the dried polymer particles. After the spray application, the polymer particles coated with surface postcrosslinker are dried thermally, and the surface postcrosslinking reaction can take place either before or during the drying.

The spray application of a solution of the surface postcrosslinker is preferably performed in mixers with moving mixing tools, such as screw mixers, disk mixers and paddle mixers.

Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® plowshare mixers (Gebr. Lödige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; USA) and Schugi Flexomix® (Hosokawa Micron BV; Doetinchem; the Netherlands). However, it is also possible to spray on the surface postcrosslinker solution in a fluidized bed.

The surface postcrosslinkers are typically used in the form of an aqueous solution. The penetration depth of the surface postcrosslinker into the polymer particles can be adjusted via the content of nonaqueous solvent and total amount of solvent.

When exclusively water is used as the solvent, a surfactant is advantageously added. This improves the wetting characteristics and reduces the tendency to form lumps. However, preference is given to using solvent mixtures, for example isopropanol/water, 1,3-propanediol/water and propylene glycol/water, where the mixing ratio in terms of mass is preferably from 20:80 to 40:60.

The thermal drying is preferably carried out in contact driers, more preferably paddle driers, most preferably disk driers. Suitable driers are, for example, Hosokawa Bepex® Horizontal Paddle Dryers (Hosokawa Micron GmbH; Leingarten; Germany), Hosokawa Bepex® Disc Dryers (Hosokawa Micron GmbH; Leingarten; Germany), Holo-Flite® driers (Metso Minerals Industries Inc.; Danville; USA) and Nara Paddle Dryers (NARA Machinery Europe; Frechen; Germany). Moreover, fluidized bed driers may also be used.

The drying can be effected in the mixer itself, by heating the jacket or blowing in warm air. Equally suitable is a downstream drier, for example a shelf drier, a rotary tube oven or a heatable screw. It is particularly advantageous to effect mixing and drying in a fluidized bed drier.

Preferred drying temperatures are in the range of 100 to 250° C., preferably 120 to 220° C., more preferably 130 to 210° C. and most preferably 150 to 200° C. The preferred residence time at this temperature in the reaction mixer or drier is preferably at least 10 minutes, more preferably at least 20 minutes, most preferably at least 30 minutes, and typically at most 60 minutes.

In a preferred embodiment of the present invention, the water-absorbing polymer particles are cooled after the thermal drying. The cooling is preferably performed in contact coolers, more preferably paddle coolers and most preferably disk coolers. Suitable coolers are, for example, Hosokawa Bepex® Horizontal Paddle Coolers (Hosokawa Micron GmbH; Leingarten; Germany), Hosokawa Bepex® Disc Coolers (Hosokawa Micron GmbH; Leingarten; Germany), Holo-Flite® coolers (Metso Minerals Industries Inc.; Danville; USA) and Nara Paddle Coolers (NARA Machinery Europe; Frechen; Germany). Moreover, fluidized bed coolers may also be used.

In the cooler, the water-absorbing polymer particles are cooled to 20 to 150° C., preferably 30 to 120° C., more preferably 40 to 100° C. and most preferably 50 to 80° C.

Subsequently, the surface postcrosslinked polymer particles can be classified again, excessively small and/or excessively large polymer particles being removed and recycled into the process.

To further improve the properties, the surface postcrosslinked polymer particles can be coated or remoisturized.

The remoisturizing is preferably performed at 30 to 80° C., more preferably at 35 to 70° C., most preferably at 40 to 60° C. At excessively low temperatures, the water-absorbing polymer particles tend to form lumps, and, at higher temperatures, water already evaporates to a noticeable degree. The amount of water used for remoisturizing is preferably from 1 to 10% by weight, more preferably from 2 to 8% by weight and most preferably from 3 to 5% by weight, based in each case on the water-absorbing polymer particles. The remoisturizing increases the mechanical stability of the polymer particles and reduces their tendency to static charging. The remoisturizing is advantageously performed in the cooler after the thermal drying.

Suitable coatings for improving the free swell rate and the permeability (SFC) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, and surfactants, such as Span® 20.

The present application further provides an aqueous acrylic acid prepared by the process according to the invention, wherein the aqueous 3-hydroxypropionic acid has been prepared by fermentation.

The present application further provides the aqueous acrylic acid removed from the dehydration.

The inventive aqueous acrylic acid preferably comprises water and
20 to 80% by weight of acrylic acid,
0.001 to 1% by weight of formic acid,
0.001 to 1% by weight of acetic acid,
0.001 to 1% by weight of glycolic acid,
0.0001 to 0.05% by weight of formaldehyde,
0.0001 to 0.05% by weight of acetaldehyde,
0.0001 to 0.05% by weight of methanol,
0.0001 to 0.05% by weight of ethanol and
0.0001 to 0.1% by weight of an inert organic solvent 1.

The inventive aqueous acrylic acid more preferably comprises water and
30 to 70% by weight of acrylic acid,
0.005 to 0.5% by weight of formic acid,
0.005 to 0.5% by weight of acetic acid,
0.005 to 0.5% by weight of glycolic acid,
0.0002 to 0.02% by weight of formaldehyde,
0.0002 to 0.02% by weight of acetaldehyde,
0.0002 to 0.02% by weight of methanol,
0.0002 to 0.02% by weight of ethanol and
0.0005 to 0.05% by weight of an inert organic solvent 1.

The inventive aqueous acrylic acid most preferably comprises water and
40 to 60% by weight of acrylic acid,
0.01 to 0.1% by weight of formic acid,
0.01 to 0.1% by weight of acetic acid, 0.01 to 0.1% by weight of glycolic acid,
0.0005 to 0.01% by weight of formaldehyde,
0.0005 to 0.01% by weight of acetaldehyde,
0.0005 to 0.01% by weight of methanol,
0.0005 to 0.01% by weight of ethanol and
0.001 to 0.02% by weight of an inert organic solvent 1.

The inert organic solvent is preferably selected from dimethyl phthalate, diethyl phthalate, dimethyl isophthalate, diethyl isophthalate, dimethyl terephthalate, diethyl terephthalate, nonanoic acid, decanoic acid, biphenyl and/or diphenyl ether.

Methods

Determination of the 3-Hydroxypropionic Acid and Acrylic Acid Contents

The 3-hydroxypropionic acid and acrylic acid contents are determined by reverse phase chromatography with ultraviolet detection.

The sample is prepared by weighing about 100 to 300 mg of sample into a 50 ml standard flask and making it up to the mark with eluent A. Eluent A is a mixture of 1000 ml of water and 1 ml of 0.5 molar sulfuric acid.

For calibration of 3-hydroxypropionic acid, four weights (about 280 mg, 180 mg, 90 mg and 60 mg) are used, with acidification (possibly re-acidification) to a pH of 3 to 4 with about 100 µl of 25% by weight sulfuric acid before making up to the mark of the 50 ml standard flask. The calibration range is 0.1 to 280 mg/50 ml.

For calibration of acrylic acid, at least two weights are diluted to at least six concentrations. The calibration range is 0.01 to 0.9 mg/50 ml.

For reverse phase chromatography, a separating column of the Prontosil 120-3-C18 AQ 3 µm, 150×4.6 mm type (BISCHOFF Analysentechnik und-geräte GmbH, Leonberg, Germany) is used. The temperature is 25° C., the injection volume is 50 µl, the flow rate is 1.5 ml/min and the run time is 15 minutes. The UV detector is set to 205 nm. From the start to 8 minutes 100% by weight of eluent A is used, from 8 to 11.5 minutes a mixture of 40% by weight of eluent A and 60% by weight of eluent B, and from 11.5 minutes to the end 100% by weight of eluent A. Eluent B is acetonitrile.

Determination of the Oligomeric 3-Hydroxypropionic Acid and Oligomeric Acrylic Acid Contents The oligomeric 3-hydroxypropionic acid and oligomeric acrylic acid contents are determined by ion exclusion chromatography with refractive index detection.

To prepare the samples, the components to be analyzed are separated from the sample matrix by means of a solid phase extraction. For this purpose, an SPE cartridge of the Bakerband SiOH 6 ml, 1000 mg (J. T. Baker, Avantor Performance Materials, Inc., Center Valley, Pa., USA) type is used. The SPE cartridge is activated with 6 ml of methanol and flushed twice with 6 ml each time of eluent. The SPE cartridge must never run dry. Subsequently, the sample is pipetted onto the SPE cartridge and flushed 10 times with 1 ml of eluent each time into a 10 ml standard flask. The amount of sample used is 65 µl in the case of bottoms samples, 85 µl in the case of tops samples and 75 µl in the case of extract samples. Unless the samples comprise hydrophobic solvent (inert organic solvent 1, inert organic solvent 2), these samples can be applied without extraction; for this purpose, 85 µl are dissolved directly in 10 ml of eluent. The eluent used is 0.1% by volume aqueous phosphoric acid.

For ion exclusion chromatography, two separating columns of the Shodex RSpak KC-811, 300×8 mm (SHOWA DENKO K.K. Shodex (Separation & HPLC) Group, Kawasaki, Japan) type are used connected in series. The temperature is 40° C., the injection volume is 100 µl, the flow rate is 1.0 ml/min and the run time is 45 minutes. The eluent used is 0.1% by weight aqueous phosphoric acid. The autosampler is cooled to 15° C.

For evaluation, the integration is preceded by a blank value subtraction. For this purpose, eluent is injected and the chromatogram thus obtained is subtracted from the sample chromatogram. The evaluation is effected in terms of area percent, with conversion to percent by weight by means of the following formula:

$$\text{Weight \% (Oligomer)} = \frac{\text{Weight \% (monomer)}}{\text{Area \% (monomer)}} \times \text{Area \% (oligomer)}$$

To evaluate the oligomers, the contents of the dimers, trimers, tetramers and pentamers (i.e. n=2 to 5) are added up in each case. The retention times are monitored by injecting 3-hydroxypropionic acid and diacrylic acid.

EXAMPLES

Example 1

A jacketed 2 l three-neck flask with distillation attachment was initially charged with 1500 g of an about 30% by weight aqueous 3-hydroxypropionic acid, water was distilled off at 100 mbar for 3 hours and the remaining residue was distilled at 40 mbar. The jacket was heated by means of heat transfer oil. The composition of distillate and distillation residue was analyzed.

TABLE 1

Composition of the distillate

| Time [h] | 3HPA [% by weight] | AA [% by weight] | Oligo-3HPA [% by weight] | Oligo-AA [% by weight] |
|---|---|---|---|---|
| 2.9 | 36.5 | 9.3 | 2.1 | 0.0 |
| 5.5 | 38.2 | 19.4 | 6.3 | 1.6 |
| 6.7 | 12.1 | 51.5 | 6.0 | 20.2 |
| 7.6 | 2.2 | 62.1 | 5.8 | 26.8 |
| 8.8 | 0.5 | 57.6 | 0.2 | 41.4 |

TABLE 2

Composition of the distillation residue

| Time [h] | Temperature [° C.] | 3HPA [% by weight] | AA [% by weight] | Oligo-3HPA [% by weight] | Oligo-AA [% by weight] |
|---|---|---|---|---|---|
| 2.9 | 154 | 42.3 | 0.2 | 41.5 | 9.3 |
| 5.5 | 180 | 16.3 | 0.2 | 55.9 | 21.5 |
| 6.7 | 221 | 1.7 | 0.3 | 56.9 | 37.7 |
| 7.6 | 224 | 0.3 | 0.3 | 38.0 | 59.7 |
| 8.8 | 230 | 0.1 | 0.4 | 31.2 | 58.1 |

3HPA 3-hydroxypropionic acid
AA acrylic acid
Oligo-3HPA oligomeric 3-hydroxypropionic acid
Oligo-AA oligomeric acrylic acid The results show that, in the distillation residue, 3-hydroxypropionic acid is first converted to oligomeric 3-hydroxypropionic acid. Only thereafter is there significant formation of acrylic acid and oligomeric acrylic acid. The dehydration of 3-hydroxypropionic acid probably proceeds via oligomeric 3-hydroxypropionic acid as an intermediate. For a high yield and a high selectivity, 3-hydroxypropionic acid therefore has to be converted to oligomeric 3-hydroxypropionic acid. Thus, residence times sufficient for dehydration are necessary.

Example 2

The dehydration (1) was performed in a reactor with a forced-circulation flash evaporator and attached rectification column 1.

The reactor used was a 3 l jacketed glass vessel. The amount of liquid in the reactor was about 2500 g. This corresponds to a residence time of about 5 hours. The temperature in the reactor was 160° C. The reactor was simultaneously the bottom of the rectification column 1.

The forced-circulation flash evaporator consisted of a pump, a heat exchanger and a pressure-retaining valve. The reactor contents were circulated through the heat exchanger and the pressure-retaining valve by means of the pump. The heat exchanger consisted of 2 jacketed tubes having a length of 1000 mm and an inner area of 0.074 m$^2$.

The rectification column was electrically trace-heated and had an internal diameter of 50 mm. The separating internals used were Rhombopak 9M fabric packings (Sulzer Chemtech, Winterthur, Switzerland). The height of the fabric packings was 500 mm. The vapors were condensed in two stages and separated by means of a decanter into an organic phase and an aqueous phase.

The aqueous solution used for dehydration comprised
76.5% by weight of water,
0.02% by weight of acrylic acid,
0.32% by weight of oligomeric acrylic acid,
19.9% by weight of 3-hydroxypropionic acid and
3.24% by weight of oligomeric 3-hydroxypropionic acid.

500 g/h of the aqueous solution and 25 g/h of a mixture of 94% by weight of dimethyl phthalate and 6% by weight of pentamethyldiethylenetriamine were preheated to 48° C. and metered in upstream of the heat exchanger of the forced-circulation flash evaporator.

A further 249 kg/h of reactor contents were circulated through the forced-circulation flash evaporator. Upstream of the pressure-retaining valve, the pressure was 1.608 bar and the temperature was 168° C. 27 g/h of reactor contents were discharged from the circuit and discarded.

The discharged reactor contents comprised
1.5% by weight of water,
7.2% by weight of acrylic acid,
12.8% by weight of oligomeric acrylic acid,
1.1% by weight of 3-hydroxypropionic acid and
8.7% by weight of oligomeric 3-hydroxypropionic acid.

The temperature at the top of the rectification column 1 was 108° C. The vapor was cooled directly in a first cooler with 5 kg/h of aqueous phase from the decanter. The offgas from the first cooler was cooled indirectly in a second cooler (post-cooler). The offgas from the second cooler had a temperature of 24° C. and a pressure of 949 mbar.

From the decanter, 2.0 l/h of aqueous phase as reflux were recycled into the rectification column 1, and 524 g/h were discharged as product. The organic phase was metered in beyond the pump of the forced-circulation flash evaporator.

The discharged aqueous phase comprised
76.2% by weight of water,
21.8% by weight of acrylic acid,
0.8% by weight of oligomeric acrylic acid,
0.1% by weight of 3-hydroxypropionic acid and
1.1% by weight of dimethyl phthalate.

25 g/h of an aqueous acrylic acid were metered into the decanter. The aqueous acrylic acid comprised 49% by weight of water, 49% by weight of acrylic acid, 1% by weight of phenothiazine and 1% by weight of hydroquinone monomethyl ether. The aqueous acrylic acid still comprised undissolved fractions, probably phenothiazine.

Example 3

The dehydration (1) is performed in a jacketed 10 l glass vessel. Via a base outlet, the contents of the glass vessel are circulated by means of a pump through a shell-and-tube heat exchanger. The glass vessel is initially charged with 4000 g of a mixture of 85% by weight of diphyl and 15% by weight of pentamethyldiethylenetriamine. Diphyl is the eutectic mixture of diphenyl ether and biphenyl. The glass vessel is about 80% full in the steady state. Below the shell-and-tube heat exchanger, 2 l/h of air are metered into the circuit.

The feed used is 1571 g/h of aqueous 3-hydroxypropionic acid, prepared according to WO 2012/074818 A2. The aqueous 3-hydroxypropionic acid has the following composition:
45.0% by weight of 3-hydroxypropionic acid,
12.0% by weight of oligomeric 3-hydroxypropionic acid,
40.7% by weight of water,
2.0% by weight of acrylic acid,
0.1% by weight of oligomeric acrylic acid,
0.06% by weight of glycolic acid,
0.05% by weight of 2-hydroxypropionic acid,
0.02% by weight of formic acid,
0.02% by weight of acetic acid,
0.02% by weight of succinic acid,
0.02% by weight of fumaric acid,
0.004% by weight of formaldehyde,
0.002% by weight of acetaldehyde,
0.002% by weight of methanol and
0.002% by weight of ethanol The reaction temperature in the glass vessel is 180° C.; the pressure in the glass vessel is 950 mbar.

20.8 g/h of residue are withdrawn from the glass vessel. The residue is extracted with 25.0 g/h of water and the organic phase is recycled into the glass vessel. Losses of diphyl and pentamethyldiethylenetriamine are replaced regularly. The target values in the liquid phase for diphyl and pentamethyldiethylenetriamine are about 40% by weight and about 8% by weight. The aqueous phase is sent to the extraction (2).

A 25-tray bubble-cap tray column having an internal diameter of 50 mm is placed atop the glass vessel. The bubble-cap tray column has an electrical guard heater.

Between the 20th and 21st trays of the bubble-cap tray column is installed a collecting tray. The liquid is withdrawn completely therefrom and conveyed by means of a pump through a heat exchanger, in the course of which it is cooled to 35° C., and is recycled to the 25th tray of the bubble-cap tray column. 1557 g/h of the cooled liquid are sent to the extraction (2). 493 g/h of the cooled liquid are recycled to the 20th tray of the bubble-cap tray column. The reflux is stabilized with 0.005% by weight of phenothiazine.

The liquid withdrawn from the 20th tray of the bubble-cap tray column has the following composition:
<0.0001% by weight of 3-hydroxypropionic acid,
<0.0001% by weight of oligomeric 3-hydroxypropionic acid,
51.2% by weight of water,
48.7% by weight of acrylic acid,
<0.0001% by weight of oligomeric acrylic acid,
0.045% by weight of glycolic acid,
<0.0001% by weight of 2-hydroxypropionic acid, 0.02% by weight of formic acid,
0.02% by weight of acetic acid,
<0.0001% by weight of succinic acid,
<0.0001% by weight of fumaric acid,
0.003% by weight of formaldehyde,
<0.0001% by weight of acetaldehyde,
0.001% by weight of methanol,
0.001% by weight of ethanol,
<0.0001% by weight of pentamethyldiethylenetriamine and
0.01% by weight of diphyl The extraction (2) is performed in a 20-tray sieve tray column having an internal diameter of 50 mm. The aqueous phases from the dehydration (1) are heated to 50° C. and sent to the sieve tray column at the base. The feed of aqueous phase totals 2830 g/h. At the top of the sieve tray column, 2809 g/h of liquid from the bottom of the distillation (3) and 21 g/h of dimethyl phthalate with a temperature of 50° C. as extractant are fed in.

1024 g/h of the aqueous extract withdrawn at the top of the sieve tray column are recycled at the base of the sieve tray column. The rest of the aqueous extract is discarded.

The aqueous extract withdrawn at the top of the sieve tray column has the following composition:
0.02% by weight of 3-hydroxypropionic acid,
0.3% by weight of oligomeric 3-hydroxypropionic acid,
96.8% by weight of water,
0.6% by weight of acrylic acid,
0.5% by weight of oligomeric acrylic acid,
0.1% by weight of glycolic acid,
0.1% by weight of 2-hydroxypropionic acid,
0.05% by weight of formic acid,
0.025% by weight of acetic acid,
0.05% by weight of succinic acid,
0.05% by weight of fumaric acid,
0.0035% by weight of formaldehyde,
<0.0001% by weight of acetaldehyde,
0.001% by weight of methanol,
0.0003% by weight of ethanol,
0.2% by weight of pentamethyldiethylenetriamine,
0.0002% by weight of diphyl and
1.2% by weight of dimethyl phthalate At the base of the sieve tray column, 3799 g/h of organic extract are withdrawn and transferred into the distillation (3).

The organic extract withdrawn at the base of the sieve tray column has the following composition:
0.002% by weight of 3-hydroxypropionic acid,
0.1% by weight of oligomeric 3-hydroxypropionic acid,
3.7% by weight of water,
22.2% by weight of acrylic acid,
0.5% by weight of oligomeric acrylic acid,
0.06% by weight of glycolic acid,
0.035% by weight of 2-hydroxypropionic acid,
0.006% by weight of formic acid,
0.02% by weight of acetic acid,
0.005% by weight of succinic acid,
0.008% by weight of fumaric acid,
0.002% by weight of formaldehyde,
0.0005% by weight of acetaldehyde,
0.0005% by weight of methanol,
0.001% by weight of ethanol and
0.06% by weight of pentamethyldiethylenetriamine,
1.5% by weight of diphyl and
71.8% by weight of dimethyl phthalate The distillation (3) is performed in a 30-tray bubble-cap tray column having an internal diameter of 50 mm. The bubble-cap tray column has an electrical guard heater.

The feed to the distillation (3) is heated to 160° C. and fed to the 5th tray of the bubble-cap tray column.

The bottoms liquid of the bubble-cap tray column is circulated by means of a pump through a shell-and-tube heat exchanger. Below the shell-and-tube heat exchanger, 2 l/h of air are metered into the circuit. The temperature and pressure in the bottom of the bubble-cap tray column are 220° C. and 265 mbar.

2809 g/h of liquid are withdrawn from the bottom of the bubble-cap tray column and recycled into the extraction (2). A further 11 g/h of liquid are discharged from the bottom of the bubble-cap tray column and discarded.

The liquid withdrawn from the bottom of the bubble-cap tray column has the following composition:
0.003% by weight of 3-hydroxypropionic acid,
0.2% by weight of oligomeric 3-hydroxypropionic acid,
<0.0001% by weight of water,
0.2% by weight of acrylic acid,
0.6% by weight of oligomeric acrylic acid,
0.07% by weight of glycolic acid,
0.03% by weight of 2-hydroxypropionic acid,
<0.0001% by weight of formic acid,
<0.0001% by weight of acetic acid,
0.007% by weight of succinic acid,
0.02% by weight of fumaric acid,
<0.0001% by weight of formaldehyde,
<0.0001% by weight of acetaldehyde,
<0.0001% by weight of methanol,
<0.0001% by weight of ethanol and
0.07% by weight of pentamethyldiethylenetriamine,
2.0% by weight of diphyl and
96.8% by weight of dimethyl phthalate Between the 15th and 16th trays of the bubble-cap tray column is installed a collecting tray. The liquid is withdrawn completely therefrom and conveyed by means of a pump through a heat exchanger, in the course of which it is cooled to 65° C., and is recycled to the 20th tray of the bubble-cap tray column. 750 g/h of the cooled liquid are withdrawn as crude acrylic acid. 1379 g/h of the cooled liquid are recycled to the 15th tray of the bubble-cap tray column.

The crude acrylic acid has the following composition:
<0.0001% by weight of 3-hydroxypropionic acid,
<0.0001% by weight of oligomeric 3-hydroxypropionic acid,
3.5% by weight of water,
96.4% by weight of acrylic acid,
<0.0001% by weight of oligomeric acrylic acid,
0.0075% by weight of glycolic acid,
<0.0001% by weight of 2-hydroxypropionic acid,
0.02% by weight of formic acid,
0.07% by weight of acetic acid,
<0.0001% by weight of succinic acid,
<0.0001% by weight of fumaric acid,
<0.0001% by weight of formaldehyde,
<0.0001% by weight of acetaldehyde,
0.0005% by weight of methanol,
0.002% by weight of ethanol and
<0.0001% by weight of pentamethyldiethylenetriamine,
<0.0001% by weight of diphyl and
<0.0001% by weight of dimethyl phthalate Between the 25th and 26th trays of the bubble-cap tray column is installed a collecting tray. The liquid is withdrawn completely therefrom and conveyed by means of a pump through a heat exchanger, in the course of which it is cooled to 25° C., and is recycled to the 30th tray of the bubble-cap tray column. 213 g/h of the cooled liquid are recycled into the extraction (2). 161 g/h of the cooled liquid are recycled to the 25th tray of the bubble-cap tray column. The reflux is stabilized with 0.005% by weight of phenothiazine. The pressure at the top of the bubble-cap tray column is 100 mbar.

The liquid withdrawn from the 25th tray of the bubble-cap tray column has the following composition:
<0.0001% by weight of 3-hydroxypropionic acid,
<0.0001% by weight of oligomeric 3-hydroxypropionic acid,
59.7% by weight of water,
40.0% by weight of acrylic acid,
<0.0001% by weight of oligomeric acrylic acid,
<0.0001% by weight of glycolic acid,
<0.0001% by weight of 2-hydroxypropionic acid,
0.14% by weight of formic acid,
0.15% by weight of acetic acid,
<0.0001% by weight of succinic acid,
<0.0001% by weight of fumaric acid,
0.002% by weight of formaldehyde,
0.001% by weight of acetaldehyde,
0.006% by weight of methanol,
0.001% by weight of ethanol and
<0.0001% by weight of pentamethyldiethylenetriamine,
<0.0001% by weight of diphyl and
<0.0001% by weight of dimethyl phthalate The example shows that the acrylic acid prepared from renewable raw materials can be purified by the process according to the invention in a simple manner and with high yield.

The invention claimed is:

1. A process for continuously dehydrating aqueous 3-hydroxypropionic acid to aqueous acrylic acid in a liquid phase comprising preheating the aqueous 3-hydroxypropionic acid to a temperature of 30 to 100° C., continuously adding the preheated aqueous 3-hydroxypropionic acid to the liquid phase, the liquid phase having a temperature of 120 to 250° C., and continuously withdrawing the aqueous acrylic acid from the liquid phase, wherein a weight ratio of oligomeric 3-hydroxypropionic acid to monomeric 3-hydroxypropionic acid in the aqueous 3-hydroxypropionic acid is at least 1:20, and
wherein a weight ratio of oligomeric 3-hydroxypropionic acid to monomeric 3-hydroxypropionic acid in the liquid phase is at least 1:1.

2. The process according to claim 1, wherein a residence time in the liquid phase is at least 10 minutes.

3. The process according to claim 1, wherein the liquid phase has a temperature of 130 to 220° C.

4. The process according to claim 1, wherein the dehydration is base- or acid-catalyzed.

5. The process according to claim 1, wherein the liquid phase comprises 5 to 95% by weight of an inert organic solvent and the inert organic solvent has a solubility in water at 23° C. of less than 1 g per 100 ml of water.

6. The process according to claim 5, wherein the inert organic solvent at a pressure of 1013 mbar has a boiling point of 200 to 350° C.

7. The process according to claim 5, wherein the inert organic solvent is selected from the group consisting of dimethyl phthalate, diethyl phthalate, dimethyl isophthalate, diethyl isophthalate, dimethyl terephthalate, diethyl terephthalate, nonanoic acid, decanoic acid, biphenyl, diphenyl ether, and mixtures thereof.

8. The process according to claim 1, wherein water and acrylic acid are removed by distillation from the liquid phase.

9. The process according to claim 8, wherein distillation is effected with a rectification column.

10. The process according to claim 1, wherein a space-time yield is from 10 to 100 kg/h of acrylic acid per $m^3$ of liquid phase.

11. The process according to claim 1, wherein a polymerization inhibitor 1 is added to the liquid phase.

12. The process according to claim 11, wherein the polymerization inhibitor 1 is selected from the group consisting of phenothiazine, hydroquinone, hydroquinone monomethyl ether, and mixtures thereof.

13. The process according to claim 1, wherein a polymerization inhibitor 2 is added to the obtained water/acrylic acid mixture.

14. The process according to claim 13, wherein the polymerization inhibitor 2 is selected from the group consisting of phenothiazine, hydroquinone, hydroquinone monomethyl ether, and mixtures thereof.

15. The process according to claim 1, wherein the weight ratio of oligomeric 3-hydroxypropionic acid to monomeric 3-hydroxypropionic acid in the aqueous 3-hydroxypropionic acid is at least 1:10.

16. The process according to claim 1, wherein the weight ratio of oligomeric 3-hydroxypropionic acid to monomeric 3-hydroxypropionic acid in the aqueous 3-hydroxypropionic acid is at least 1:5.

17. A process for continuously dehydrating aqueous 3-hydroxypropionic acid to aqueous acrylic acid in a liquid phase comprising preheating the aqueous 3-hydroxypropionic acid to a temperature of 30 to 100° C., continuously adding the preheated aqueous 3-hydroxypropionic acid to the liquid phase, the liquid phase having a temperature of 120-250° C., and continuously withdrawing the aqueous acrylic acid from the liquid phase, wherein a weight ratio of oligomeric 3-hydroxypropionic acid to monomeric 3-hydroxypropionic acid in the liquid phase is at least 1:1.

18. The method of claim 17, wherein the weight ratio of oligomeric 3-hydroxypropionic acid to monomeric 3-hydroxypropionic acid in the liquid phase is at least 3:1.

19. The method of claim 17, wherein the weight ratio of oligomeric 3-hydroxypropionic acid to monomeric 3-hydroxypropionic acid in the liquid phase is at least 5:1.

20. The method of claim 17, wherein the weight ratio of oligomeric 3-hydroxypropionic acid to monomeric 3-hydroxypropionic acid in the liquid phase is at least 10:1.

21. The method of claim 1, wherein the aqueous 3-hydroxypropionic acid is preheated to a temperature of 40 to 95° C.

22. The method of claim 1, wherein the aqueous 3-hydroxypropionic acid is preheated to a temperature of 50 to 90° C.

* * * * *